(12) United States Patent  (10) Patent No.: US 8,790,251 B2
Yamaguchi  (45) Date of Patent: Jul. 29, 2014

(54) ELECTRONIC ENDOSCOPE SYSTEM AND PROCESSOR UNIT THEREOF, AND METHOD FOR OBTAINING BLOOD VESSEL INFORMATION

(75) Inventor: Hiroshi Yamaguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 637 days.

(21) Appl. No.: 13/016,671

(22) Filed: Jan. 28, 2011

(65) Prior Publication Data
US 2011/0237915 A1 Sep. 29, 2011

(30) Foreign Application Priority Data
Mar. 26, 2010 (JP) ................................. 2010-072065

(51) Int. Cl.
*A61B 1/06* (2006.01)
*A61B 1/00* (2006.01)
*A61B 1/04* (2006.01)

(52) U.S. Cl.
USPC ............ 600/160; 600/118; 600/178; 600/181

(58) Field of Classification Search
USPC ......... 600/109, 118, 126, 178, 323, 410, 473, 600/475, 476, 477
See application file for complete search history.

(56) References Cited

U.S. PATENT DOCUMENTS

| | | | | |
|---|---|---|---|---|
| 5,001,556 A | * | 3/1991 | Nakamura et al. | 348/70 |
| 5,512,940 A | * | 4/1996 | Takasugi et al. | 348/71 |
| 7,043,287 B1 | * | 5/2006 | Khalil et al. | 600/310 |
| 7,873,407 B2 | * | 1/2011 | Levenson et al. | 600/476 |
| 2003/0176768 A1 | | 9/2003 | Gono et al. | |
| 2005/0078175 A1 | | 4/2005 | Kaneko | |
| 2006/0276966 A1 | * | 12/2006 | Cotton et al. | 702/1 |
| 2008/0294105 A1 | * | 11/2008 | Gono et al. | 604/109 |
| 2009/0020709 A1 | * | 1/2009 | Yamaguchi et al. | 250/458.1 |
| 2009/0023991 A1 | * | 1/2009 | Gono et al. | 600/109 |

FOREIGN PATENT DOCUMENTS

| | | |
|---|---|---|
| EP | 1 484 001 A1 | 12/2004 |
| EP | 1 880 657 A1 | 1/2008 |
| JP | 2648494 B2 | 8/1997 |
| JP | 2003-334162 A | 11/2003 |
| JP | 2006-314557 A | 11/2006 |

OTHER PUBLICATIONS

Chinese Office Action, dated Mar. 5, 2014, for Chinese Application No. 201110036531.2, including an English translation.

* cited by examiner

*Primary Examiner* — Anhtuan T Nguyen
*Assistant Examiner* — William Chou
(74) *Attorney, Agent, or Firm* — Birch, Stewart, Kolasch & Birch, LLP

(57) ABSTRACT

In a special light mode, first to fourth special images are captured under first to fourth special light being narrow band light. A brightness ratio calculator extracts a blood vessel area containing a blood vessel from each special image. The brightness ratio calculator calculates first to fourth brightness ratios from the special images on every pixel within the blood vessel area. A depth and hemoglobin index calculator calculates the depth of the blood vessel and a hemoglobin index corresponding to the first and second brightness ratios, based on a correlation between the depth of the blood vessel and the hemoglobin index stored in advance. A depth and oxygen saturation calculator calculates an oxygen saturation level corresponding to the third and fourth brightness ratios, based on a correlation between the depth of the blood vessel and the oxygen saturation level stored in advance.

10 Claims, 15 Drawing Sheets

ELECTRONIC ENDOSCOPE SYSTEM AND PROCESSOR UNIT THEREOF, AND METHOD FOR OBTAINING BLOOD VESSEL INFORMATION

BACKGROUND OF THE INVENTION

1. Field of the Invention

The present invention relates to an electronic endoscope system for imaging information about a blood vessel, a processor unit for an electronic endoscope, and a method for obtaining blood vessel information.

2. Description Related to the Prior Art

In a medical field, diagnosis and treatment with use of an electronic endoscope is widely carried out in recent years. The electronic endoscope is provided with a slender insert section to be introduced into a human body cavity. The insert section contains an image sensor such as a CCD at a distal end. The electronic endoscope is connected to a light source unit. Light from the light source unit is guided through the electronic endoscope, and is emitted from the distal end of the insert section to light the inside of the body cavity. While the inside of the body cavity is irradiated with the light, the image sensor captures an image of an internal body part to be examined. The captured image is subjected to various types of processing in a processor unit connected to the electronic endoscope, and then is displayed on a monitor. The electronic endoscope can image the inside of the human body cavity in real time, and facilitates the precise diagnosis and the effective treatment.

In the light source unit, a white light source such as a xenon lamp is used to emit white light (normal light), that is, broad band light having wavelengths from the blue region to the red region. The image captured under the white light shows the whole picture of the internal body part, but cannot clearly show arrangements of shallow and deep blood vessels in the interior wall, pit patterns, and irregularities in surface tissue such as a depression or lump. At clarifying such structural details, it is known that application of narrow band light (special light) having wavelengths within a specific band is effective. It is also known that the image captured under the narrow band light provides various types of information about living tissue, e.g. an oxygen saturation level in the blood vessel.

In the endoscope system according to U.S. Patent Application Publication No. 2003/0176768, for example, the image is captured whenever light of each of three primary colors of R, G, and B is applied as the narrow band light. The longer the wavelength, the deeper point the light reaches in the interior wall. Thus, the shallow or superficial blood vessel is enhanced in the image captured under the B light. The middle blood vessel is enhanced in the image captured under the G light, and the deep blood vessel is enhanced in the image captured under the R light. Also, image data of each color is subjected to color image processing, in order to produce an image in which the shallow, middle, and deep blood vessels are distinguished by different colors.

In this endoscope system, the wavelength bands of the light of each color are sharply restricted so that the bands of the light do not overlap one another. Furthermore, after the images are captured, image signals are subjected to image processing and spatial frequency filtering processing in consideration of a hemoglobin index. This allows isolation of image data at a shallow depth i.e. near the surface of the living tissue, and prevents mixing of an image of the deep blood vessel with an image of the shallow and middle blood vessels.

In Japanese Patent No. 2648494, special light IR1, IR2, and IR3 having wavelengths in the near-infrared region is used as the narrow band light. The absorbance of the special light IR1 or IR3 by the blood vessel depends on the oxygen saturation level, while the absorbance of the special light IR2 by the blood vessel does not depend thereon. The special light IR1, IR2, and IR3 is separately applied to capture three types of special images. Then, difference in brightness is calculated among the images, and the calculated brightness difference is reflected in the image in monochrome or artificial color. This image shows information about the oxygen saturation level in the blood vessel.

In the endoscopic diagnosis, it is desirable to take advantage of not only the image having the enhanced blood vessels but also the numerical blood vessel information including the hemoglobin index and the oxygen saturation level obtained from the image, for the purpose of improving diagnostic accuracy.

However, the U.S. Patent Application Publication No. 2003/0176768 does not describe determination of the hemoglobin index and the oxygen saturation level of the blood vessel, though describes the depth of the blood vessel. The Japanese Patent No. 2648494 describes determination of the oxygen saturation level, but the oxygen saturation level is calculated without consideration of the depth of the blood vessel. Therefore, the determined oxygen saturation level could be incorrect depending on the depth of the blood vessel.

SUMMARY OF THE INVENTION

An object of the present invention is to precisely determine blood vessel information including a hemoglobin index and an oxygen saturation level with consideration of the depth of a blood vessel.

To achieve the above and other objects of the present invention, an electronic endoscope system according to the present invention includes a light applying section, an image sensor, and a blood vessel information obtaining section. The light applying section applies at least three types of narrow band light having wavelengths within 400 nm to 600 nm as illumination light to an internal body part containing a blood vessel. Out of the three types of the illumination light, two types of the illumination light are narrow blue band light and narrow green band light. The image sensor captures an image of the internal body part irradiated with the illumination light. The blood vessel information obtaining section obtains blood vessel information based on a narrow band signal corresponding to the three types of the narrow band light. The blood vessel information includes the depth of the blood vessel and a hemoglobin index.

The three types of the illumination light may include first narrow blue band light, second narrow blue band light, and third narrow green band light. The narrow band signal corresponding to the three types of the narrow band light includes a first narrow blue band signal, a second narrow blue band signal, and a third narrow green band signal.

The electronic endoscope system may further include a brightness ratio calculating section and a memory. The brightness ratio calculating section calculates a first brightness ratio between the first narrow blue band signal and the second narrow blue band signal, and a second brightness ratio between the third narrow green band signal and the second narrow blue band signal. The memory stores in advance a correlation between the depth of the blood vessel and the hemoglobin index, with respect to the first and second brightness ratios. The blood vessel information obtaining section obtains based on the correlation stored in the memory the depth of the blood vessel and the hemoglobin index from the first and second brightness ratios.

The memory may store in advance a correlation between a brightness coordinate system representing the first and second brightness ratios and a blood vessel information coordinate system representing the depth of the blood vessel and the hemoglobin index. The blood vessel information obtaining section plots coordinates of the first and second brightness ratios on the brightness coordinate system, and then reads out from the blood vessel information coordinate system coordinates of the depth of the blood vessel and the hemoglobin index corresponding to the plotted coordinates, to identify values of the depth of the blood vessel and the hemoglobin index.

It is preferable that the first narrow blue band light has wavelengths of 405±10 nm, and the second narrow blue band light has wavelengths of 470±10 nm, and the third narrow green band light has wavelengths of 560±10 nm.

The light applying section may selectively emit the first narrow blue band light, the second narrow blue band light, and the third narrow green band light. The image sensor captures the image under the first narrow blue band light to obtain the first narrow blue band signal of one frame, and captures the image under the second narrow blue band light to obtain the second narrow blue band signal of one frame, and captures the image under the third narrow green band light to obtain the third narrow green band signal of one frame.

The light applying section may include a white light source for emitting white broad band light, and a wavelength band limiting section disposed between the white light source and the image sensor. The wavelength band limiting section selectively extracts the three types of the narrow band light out of the broad band light.

The wavelength band limiting section may be an acoustic-optical tunable filter. Otherwise, the wavelength band limiting section may be a rotary filter having a plurality of filters that selectively pass the three types of the narrow band light.

The illumination light may further include fourth narrow blue band light having wavelengths of 440±10 nm. An oxygen saturation level in the blood vessel is obtained as the blood vessel information from a fourth narrow blue band signal corresponding to the fourth narrow blue band light.

A processor unit according to the present invention includes a receiving section for receiving an image signal from an electronic endoscope, and a blood vessel information obtaining section. The image signal is obtained by an image sensor for capturing an image of an internal body part containing a blood vessel, while the internal body part is irradiated with at least three types of narrow band light as illumination light. Out of the three types of the illumination light, two types of the illumination light are narrow blue band light and narrow green band light. The blood vessel information obtaining section obtains blood vessel information based on a narrow band signal corresponding to the three types of the narrow band light. The blood vessel information includes the depth of the blood vessel and a hemoglobin index.

A method for obtaining blood vessel information according to the present invention includes the steps of applying at least three types of narrow band light having wavelengths within 400 nm to 600 nm as illumination light to an internal body part containing a blood vessel, capturing an image of the internal body part irradiated with the illumination light, and obtaining blood vessel information based on a narrow band signal corresponding to the three types of the narrow band light.

According to the present invention, the three types of the narrow band light are in different wavelength bands from one another within 400 nm to 600 nm, and include at least one type of blue band illumination light and at least one type of green band illumination light. The three types of the narrow band light are applied to living tissue containing the blood vessel inside a body cavity. The image of the living tissue is captured during application of the illumination light, to obtain a plurality of narrow band signals that correspond to each type of the narrow band light in the different wavelength band. The blood vessel information including the depth of the blood vessel and the hemoglobin index is obtained based on the obtained plural narrow band signals. Thus, it is possible to precisely obtain the blood vessel information such as the hemoglobin index and an oxygen saturation level, in consideration of the depth of the blood vessel.

According to the present invention, information on the shallow or superficial blood vessel is obtained with the use of the first and second narrow blue band light, and information on the deep blood vessel is obtained with the use of the third narrow green band light. Therefore, it is possible to precisely obtain the hemoglobin index of the blood vessel lying in a shallow to relatively deep (at most 500 nm) depth, which is concerned in diagnosis.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

First Embodiment

Figure 1:
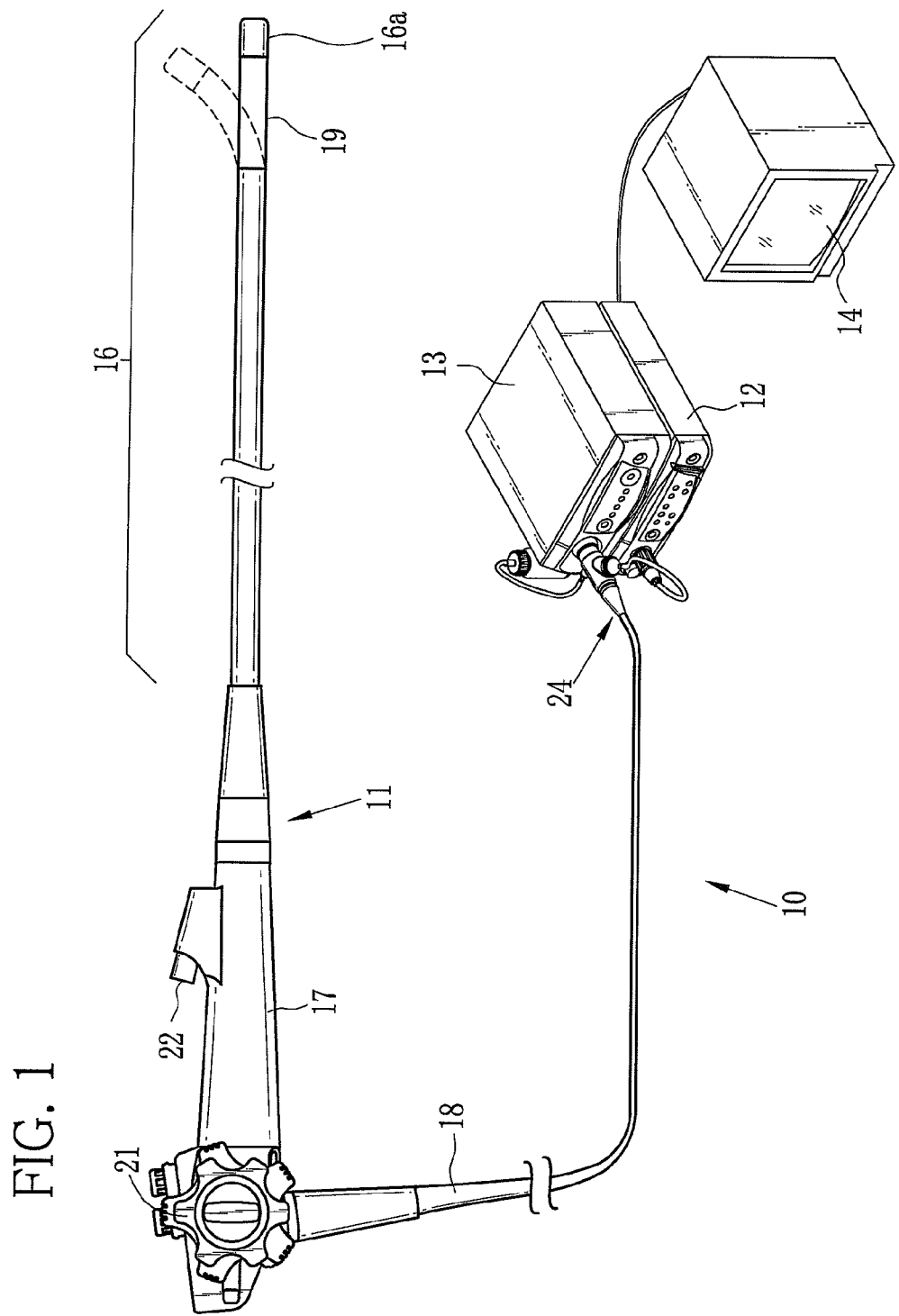
FIG. 1 is a perspective view of an electronic endoscope system according to a first embodiment.

As shown in FIG. 1, an electronic endoscope system 10 according to a first embodiment is constituted of an electronic endoscope 11 for imaging the inside of a human body cavity, a processor unit 12 that produces an endoscope image from an image signal obtained by the electronic endoscope 11, a light source unit 13 that supplies the electronic endoscope 11 with light for lighting the inside of the body cavity, and a monitor 14 for displaying the endoscope image. The electronic endoscope 11 is provided with a flexible insert section 16 to be introduced into the human body cavity, an operation section 17 disposed at a proximal end of the insert section 16, and a universal cord 18 for connecting the operation section 17 to the processor unit 12 and the light source unit 13.

The insert section 16 has a bending portion 19 at its distal end. The bending portion 19 is composed of a train of joint pieces. The bending portion 19 flexibly bends up or down or from side to side in response to operation of an angle knob 21 provided on the operation section 17. The bending portion 19 is provided with a distal end portion 16a that has the function of imaging. The distal end portion 16a is aimed at a desired direction inside the body cavity by flexibly bending the bending portion 19.

A connector 24 is attached to an end of the universal cord 18. The connector 24 is a complex connector that has a communication connector to be coupled to the processor unit 12 and a lighting connector to be coupled to the light source unit 13. The electronic endoscope 11 is detachably connected to the processor unit 12 and the light source unit 13 via the connector 24.

Figure 2:
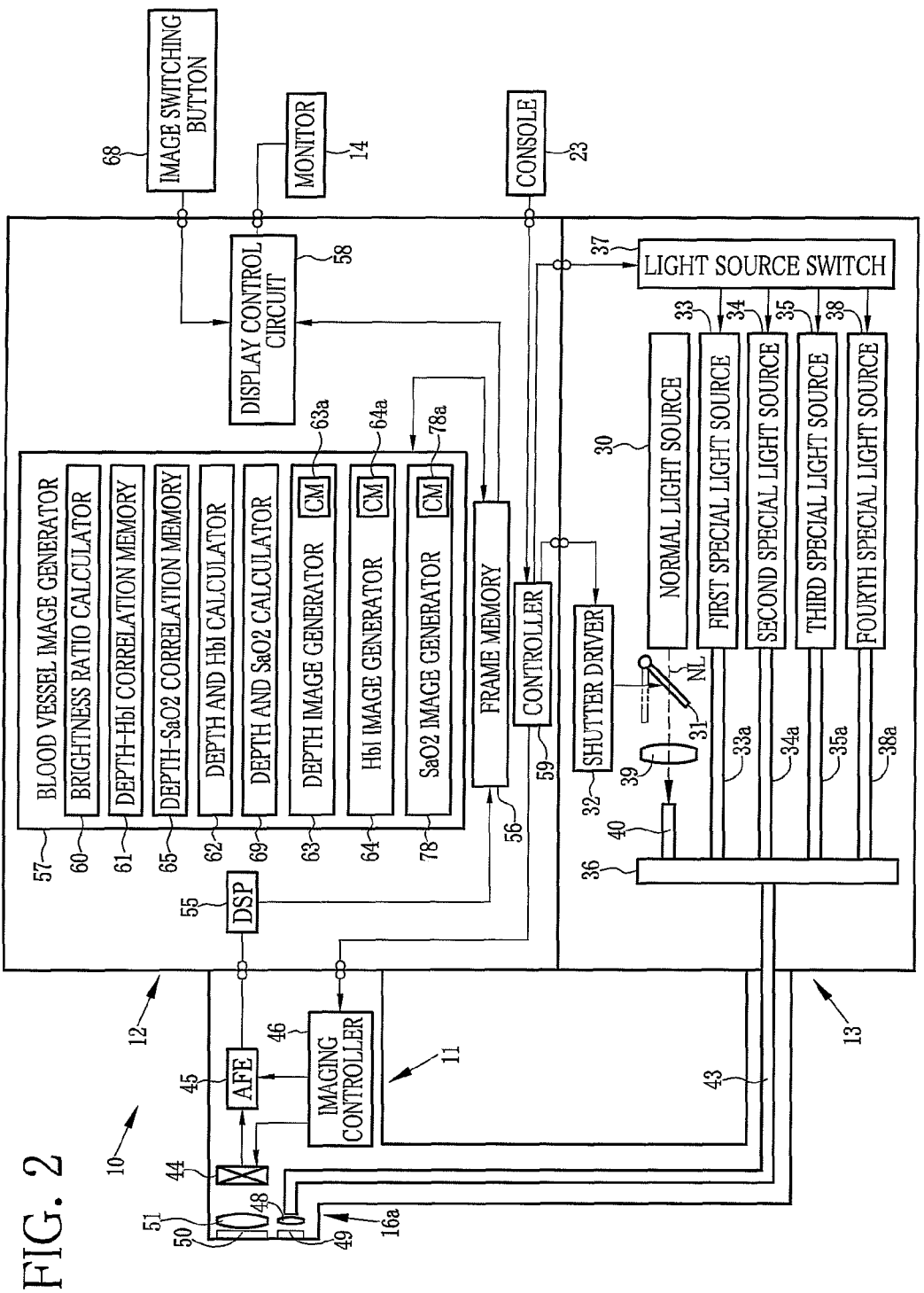
FIG. 2 is a block diagram of the electronic endoscope system according to the first embodiment.

As shown in FIG. 2, the light source unit 13 is provided with a normal light source (broad band light source) 30, a shutter 31, a shutter driver 32, first to fourth special light sources (first to fourth narrow band light sources) 33 to 35 and 38, a coupler 36, and a light source switch 37. The normal light source 30 is a xenon lamp, a white LED, a micro white light source, or the like, and emits broad band light i.e. normal light (white light) NL that has wavelengths in a broadband from the red region to the blue region (approximately 470 to 700 nm). The normal light source 30 is always turned on during the use of the electronic endoscope 11. The normal light NL emitted from the normal light source 30 is converged by a condenser lens 39, and enters a normal light transmitting fiber 40.

The shutter 31 is disposed between the normal light source 30 and the condenser lens 39. The shutter 31 is movable between an insertion position in which the shutter 31 is disposed in an optical path of the normal light NL to block the normal light NL, and a retraction position in which the shutter 31 gets out of the optical path to allow the normal light NL to travel to the condenser lens 39. The shutter driver 32 is connected to a controller 59 of the processor unit 12, and controls operation of the shutter 31 based on a command from the controller 59.

Each of the first to fourth special light sources 33 to 35 and 38 is a laser diode, an LED, or the like, and emits specific narrow band light i.e. special light. The first special light source 33 emits first special light L1 in a narrow blue band having wavelengths of 400±10 nm, preferably 405 nm. The second special light source 34 emits second special light L2 in a narrow blue band having wavelengths of 470±10 nm, preferably 473 nm. The third special light source 35 emits third special light L3 in a narrow green band having wavelengths of 560±10 nm, preferably 560 nm. The fourth special light source 38 emits fourth special light L4 in a narrow blue band having wavelengths of 440±10 nm, preferably 445 nm. The first to fourth special light sources 33 to 35 and 38 are connected to special light transmitting fibers 33a to 35a and 38a, so that the first to fourth special light L1 to L4 emitted from each light source enters the first to fourth special light transmitting fibers 33a to 35a and 38a, respectively.

The coupler 36 connects the normal light transmitting fiber 40 and the first to fourth special light transmitting fibers 33a to 35a and 38a to a light guide 43, which is routed through the electronic endoscope 11. Thus, the normal light NL enters the light guide 43 through the normal light transmitting fiber 40. The first to fourth special light L1 to L4 enters the light guide 43 through the first to fourth special light transmitting fibers 33a to 35a and 38a, respectively.

The light source switch 37 is connected to the controller 59 of the processor unit 12, and turns on or off each of the first to fourth special light sources 33 to 35 and 38 based on a command from the controller 59. In the first embodiment, if the electronic endoscope system 10 is put into the normal light mode, the normal light NL is applied to the internal body part to capture a normal image, while the first to fourth special light sources 33 to 35 and 38 are turned off. If the electronic endoscope system 10 is put into the special light mode, on the other hand, the first to fourth special light sources 33 to 35 and 38 are successively turned on to capture special images, while application of the normal light NL is stopped.

To be more specific, the first special light source 33 is initially turned on by the light source switch 37. While the first special light L1 is applied to the internal body part, the image is captured. Upon completion of capturing the image, the controller 59 commands switching of the light source. Thus, the first special light source 33 is turned off, and the second special light source 34 is turned on. While the second special light L2 is applied to the internal body part, the image is captured. Upon completion of capturing the image, in a like manner, the second special light source 34 is turned off, and the third special light source 35 is turned on. While the third special light L3 is applied to the internal body part, the image is captured. Upon completion of capturing the image, the third special light source 35 is turned off, and the fourth special light source 38 is turned on. While the fourth special light L4 is applied to the internal body part, the image is captured. Upon completion of capturing the image, the fourth special light source 38 is turned off. The electronic endoscope 11 is provided with the light guide 43, a CCD 44, an analog front end processor (AFT) 45, and an imaging controller 46.

The light guide 43 is a large-diameter optical fiber, a bundle of fibers, or the like. A light entry end of the light guide 43 is inserted into the coupler 36 of the light source unit 13, and a light exit end thereof is aimed at a lighting lens 48. The normal light NL or the special light L1, L2, L3, or L4 from the light source unit 13 is guided through the light guide 43, and is incident upon the lighting lens 48. The light incident upon the lighting lens 48 is applied to the internal body part to be examined through a lighting window 49, which is attached to an end surface of the distal end portion 16a. Then, the normal light NL or the special light L1, L2, L3, or L4 is reflected from the internal body part, and is incident upon a condenser lens 51 through an imaging window 50, which is attached to the end surface of the distal end portion 16a.

The CCD 44 is a monochrome CCD that is sensitive to visible light including the normal light NL and the special light L1 to L4. The CCD 44 receives the light from the condenser lens 51 at an imaging surface 44a, and makes photoelectric conversion from the received light into signal charges and accumulates the signal charges. Then, the accumulated signal charges are read out as an image signal. The read image signal is sent to the AFE 45. The image signal obtained by the entry of the normal light NL into the CCD 44 is referred to as a normal image signal. The image signals obtained by the entry of the first to fourth special light L1 to L4 into the CCD 44 are referred to as first to fourth image signals, respectively.

The AFE 45 includes a correlated double sampling circuit (CDS), an automatic gain controller (AGC), and an analog-to-digital converter (A/D) (none of them is illustrated). The CDS applies correlated double sampling processing to the image signal outputted from the CCD 44, to remove noise due to operation of the CCD 44. The AGC amplifies the image signal after noise removal by the CDS. The A/D converts the image signal amplified by the AGC into the digital image signal of a predetermined number of bits, and inputs the digital image signal to the processor unit 12.

Figure 3A:
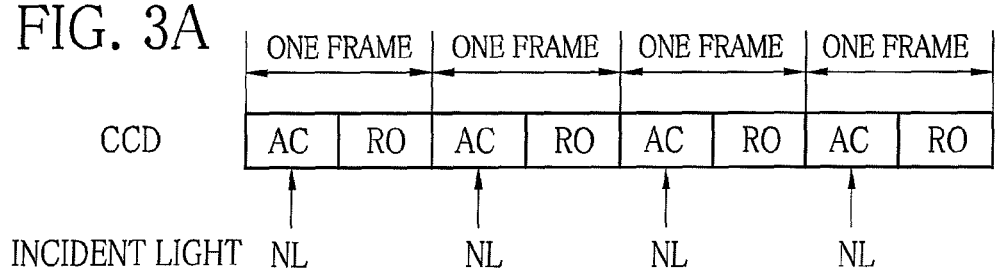
FIG. 3A is an explanatory view of imaging operation of a CCD in a normal light mode.

The imaging controller 46 is connected to the controller 59 of the processor unit 12, and sends a drive signal to the CCD 44 in response to a command from the controller 59. In response to the drive signal from the imaging controller 46, the CCD 44 outputs the image signal to the AFE 45 at a predetermined frame rate. In the normal light mode, as shown in FIG. 3A, two-step operation that includes the step of making the photoelectric conversion of the normal light NL and accumulating the signal charges and the step of reading out the accumulated signal charges as the normal image signal is carried out in a single frame. This two-step operation is repeated during the normal light mode.

Figure 3B:
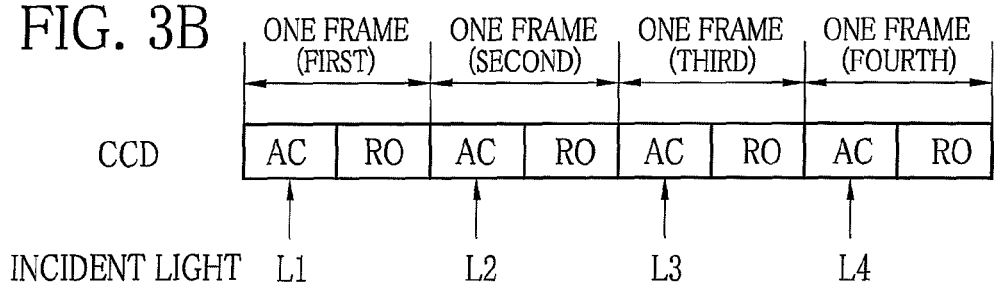
FIG. 3B is an explanatory view of imaging operation of the CCD in a special light mode.

On the other hand, in the special light mode, as shown in FIG. 3B, two-step operation that includes the step of making the photoelectric conversion of the first special light L1 and accumulating the signal charges and the step of reading out the accumulated signal charges as the first special image signal is carried out in a first frame. After completion of the readout of the first special image signal, the step of making the photoelectric conversion of the second special light L2 and accumulating the signal charges and the step of reading out the accumulated signal charges as the second special image signal are carried out in a second frame. After completion of the readout of the second special image signal, the step of making the photoelectric conversion of the third special light L3 and accumulating the signal charges and the step of reading the accumulated signal charges as the third special image signal are carried out in a third frame. After completion of the readout of the third special image signal, the step of making the photoelectric conversion of the fourth special light L4 and accumulating the signal charges and the step of reading the accumulated signal charges as the fourth special image signal are carried out in a fourth frame. These first to fourth frames are repeated.

As shown in FIG. 2, the processor unit 12 includes a digital signal processor (DSP) 55, a frame memory 56, a blood vessel image generator 57, and a display control circuit 58, and the controller 59 controls operation of each part. The DSP 55 applies color separation processing, color interpolation processing, white balance adjustment processing, gamma correction processing, and the like to the normal image signal and the first to fourth special image signals outputted from the AFE 45 of the electronic endoscope 11, to produce a normal image and first to fourth special images. The normal image and the first to fourth special images produced by the DSP 55 are written to the frame memory 56.

The blood vessel image generator 57 includes a brightness ratio calculator 60, a depth-hemoglobin index correlation memory 61, a depth-oxygen saturation correlation memory 65, a depth and hemoglobin index calculator 62, a depth and oxygen saturation calculator 69, a depth image generator 63, a hemoglobin index image generator 64, and an oxygen saturation image generator 78. The brightness ratio calculator 60 extracts a blood vessel area including a blood vessel from each of the first to fourth special images stored on the frame memory 56. The blood vessel area may be extracted based on difference in brightness between a portion of the blood vessel and the other portion, by way of example.

The brightness ratio calculator 60 calculates a first brightness ratio R1, that is, the logarithm of the brightness ratio between the first special image and the second special image (Log(B1/B2)), and a second brightness ratio R2, that is, the logarithm of the brightness ratio between the third special image and the second special image (Log(G/B2)), on pixels lying in the same position within the blood vessel area among the first to third special images. Wherein, B1 represents a brightness value of the pixel in the first special image. B2 represents the brightness value of the pixel in the second special image, and G represents the brightness value of the pixel in the third special image. The brightness ratio calculator 60 also calculates the brightness ratio (third brightness ratio) R3 between the fourth special image and the first special image (B4/B1), and the brightness ratio (fourth brightness ratio) R4 between the second special image and the first special image (B2/B1). Wherein, B4 represents the brightness value of the pixel in the fourth special image.

The depth-hemoglobin index correlation memory 61 stores the correlation among the first and second brightness ratios R1 and R2, a hemoglobin index, and the depth of the blood vessel. This correlation is obtained by analysis of a number of first to third special images accumulated in past diagnosis and the like.

Figure 4:
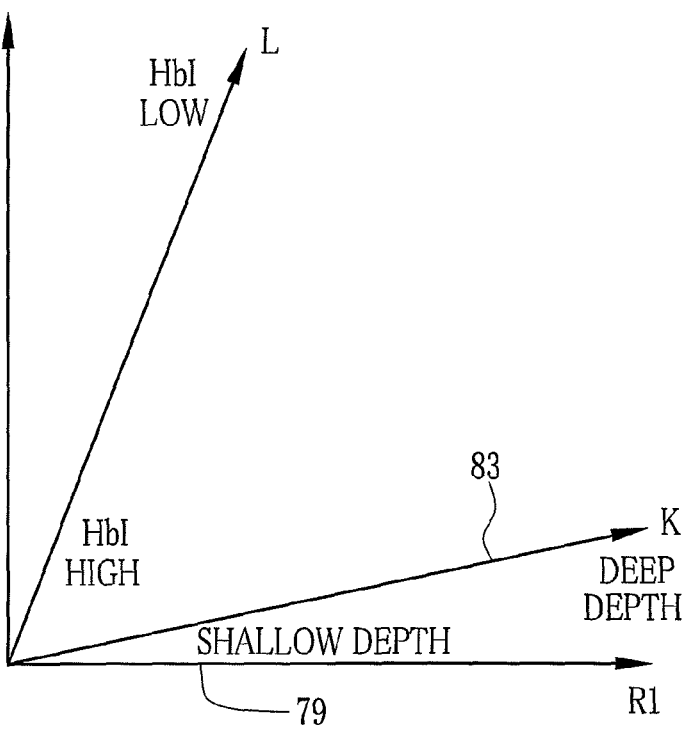
FIG. 4 is a graph showing correspondence among first and second brightness ratios R1 and R2, the depth of a blood vessel, and a hemoglobin index.

To be more specific, the depth-hemoglobin index correlation memory 61 stores the correlation between a brightness coordinate system 79 that represents the first and second brightness ratios R1 and R2 and a blood vessel information coordinate system 83 that represents the hemoglobin index and the depth of the blood vessel, as shown in FIG. 4. The blood vessel information coordinate system 83 is a KL coordinate system established in the brightness coordinate system 79. In the blood vessel information coordinate system 83, a K axis represents the depth of the blood vessel, and an L axis represents the hemoglobin index. Since the depth of the blood vessel increases with increase in the first and second brightness ratios R1 and R2, the K axis has a positive gradient to the brightness coordinate system 79. With respect to the K axis, the blood vessel becomes shallower toward the lower left, and becomes deeper toward the upper right. Since the hemoglobin index increases with increase in the first and second brightness ratios R1 and R2, the L axis has a positive gradient to the brightness coordinate system 79. With respect to the L axis, the hemoglobin index becomes higher toward the lower left, and becomes lower toward the upper right.

Figure 5:
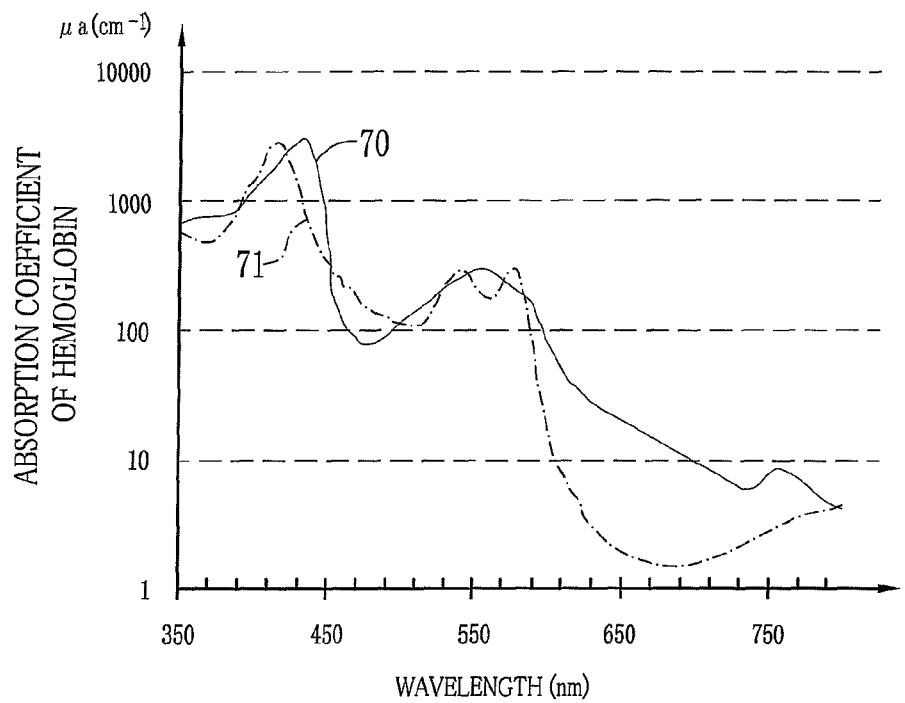
FIG. 5 is a graph showing an absorption coefficient of hemoglobin.

The depth-oxygen saturation correlation memory 65 stores the correlation among the third and fourth brightness ratios R3 and R4, an oxygen saturation level, and the depth of the blood vessel. This correlation holds if an absorption coefficient µa of hemoglobin in the blood vessel depends on a wavelength, as shown in FIG. 5, and is obtained by analysis of a number of first, second and fourth special images accumulated in past diagnosis and the like. In FIG. 5, the absorption coefficient µa represents absorbance being the degree of absorption of the light by the hemoglobin, and is a coefficient of an expression of $I_0 \exp(-\mu a \times x)$, which expresses attenuation of light applied to the hemoglobin. Wherein, $I_0$ represents the intensity of the light applied from a light source unit to living tissue, and x (cm) represents the depth of the blood vessel in the living tissue.

The reduced hemoglobin 70 that is not combined with oxygen and the oxygenated hemoglobin 71 that is combined with oxygen have different absorbance properties from each other. Thus, the reduced hemoglobin 70 and the oxygenated hemoglobin 71 show difference in the absorbance with the exceptions of equal absorbance points (intersection points of the reduced hemoglobin 70 and the oxygenated hemoglobin 71 in FIG. 5) that indicate the same absorbance (absorption coefficient µa). The difference in the absorbance brings about difference in a brightness value, even if light having the same intensity and the same wavelength is applied to the same blood vessel. Also, in a case where the two types of light having the same intensity and different wavelengths are applied, the brightness values vary with the types of the light because the absorption coefficient µa depends on the wavelength of the light.

Considering the absorbance properties of the hemoglobin as described above, it is preferable that at least one of the first, second, and fourth special lights L1, L2, and L4 has a wavelength band centered at 450 nm or less, because the absorbance varies with the oxygen saturation level at wavelengths of 445 nm and 405 nm, and the light of the short wavelength with deep reach is required to extract the information about the depth of the blood vessel. Difference in the wavelength brings about difference in the absorption coefficient and difference in the depth of reach in mucosa, irrespective of the same oxygen saturation level. Thus, it is possible to obtain the correlation between the brightness ratio and the depth of the blood vessel by taking advantage of the property of the light that the depth of reach of the light depends on the wavelength.

Figure 6:
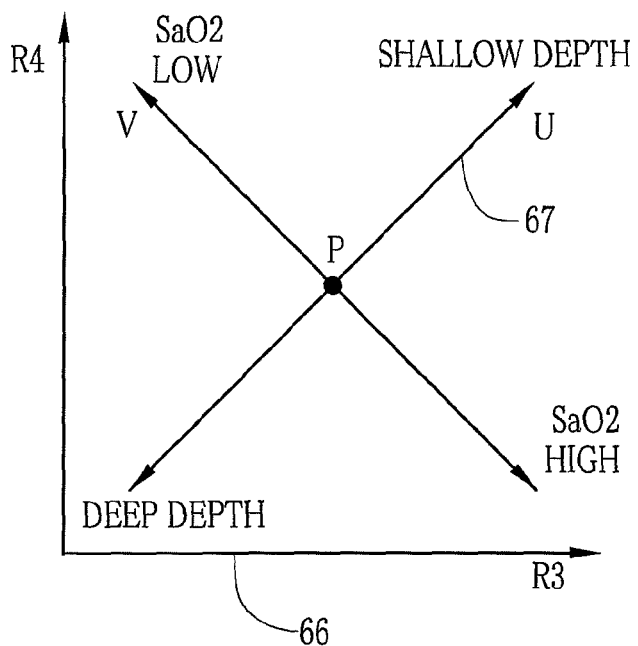
FIG. 6 is a graph showing correspondence among third and fourth brightness ratios R3 and R4, the depth of the blood vessel, and an oxygen saturation level.

The depth-oxygen saturation correlation memory 65 stores the correlation between a brightness coordinate system 66 that represents the third and fourth brightness ratios R3 and R4 and a blood vessel information coordinate system 67 that represents the oxygen saturation level and the depth of the blood vessel, as shown in FIG. 6. The blood vessel information coordinate system 67 is a UV coordinate system established on the brightness coordinate system 66. A U axis represents the depth of the blood vessel, and a V axis represents the oxygen saturation level. Since the depth of the blood vessel increases with increase in the third and fourth brightness ratios R3 and R4, the U axis has a positive gradient to the brightness coordinate system 66. With respect to the U axis, the blood vessel becomes shallower toward the upper right, and becomes deeper toward the lower left. Since the oxygen saturation level decreases with increase in the third and fourth brightness ratios R3 and R4, the V axis has a negative gradient to the brightness coordinate system 66. With respect to the V axis, the oxygen saturation level becomes lower toward the upper left, and becomes higher toward the lower right.

In the blood vessel information coordinate system 67, the U axis and the V axis intersect with each other at right angles at an intersection point P. This is because the magnitude relation of the absorbance is reversed between application of the fourth special light L4 and application of the second special light L2. In other words, as shown in FIG. 5, in application of the fourth special light L4 having the wavelengths of 440±10 nm, the absorption coefficient of the reduced hemoglobin 70 is larger than that of the oxygenated hemoglobin 71 with higher oxygen saturation level. In application of the second special light L2 having the wavelengths of 470±10 nm, on the other hand, the absorption coefficient of the oxygenated hemoglobin 71 is larger than that of the reduced hemoglobin 70. If other types of special light among which the magnitude relation of the absorbance is not reversed are applied instead of the first, second, and fourth special light L1, L2, and L4, the U and V axes do not intersect at the right angles. In application of the first special light L1 having the wavelengths of 400±10 nm, the absorption coefficient of the oxygenated hemoglobin 71 is substantially equal to that of the reduced hemoglobin 70.

Figure 7A:
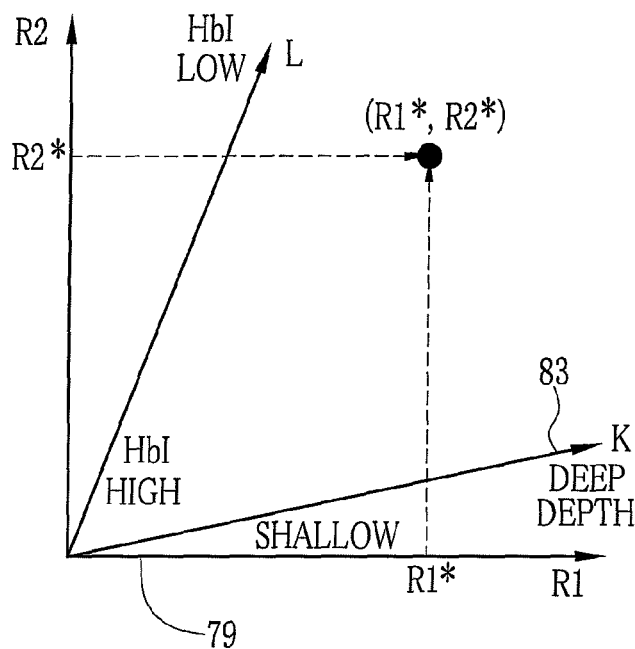
FIG. 7A is a graph in which coordinates (R1*, R2*) of the first and second brightness ratios are plotted on a brightness coordinate system.
Figure 7B:
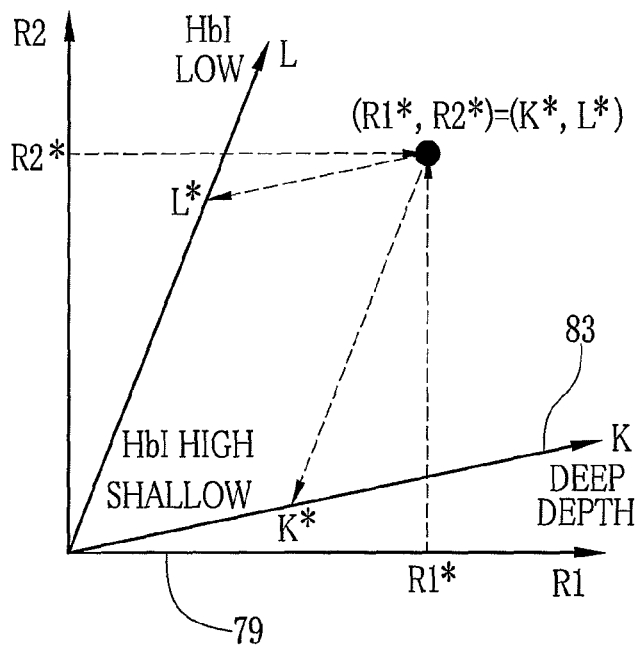
FIG. 7B is a graph that explains how to obtain coordinates (K*, L*) corresponding to the coordinates (R1*, R2*) on a blood vessel information coordinate system.

As shown in FIG. 7A, the depth and hemoglobin index calculator 62 plots in the brightness coordinate system 79 coordinates (R1*, R2*) that correspond to the first and second brightness ratios R1* and R2* being measurement values. After the plot of the coordinates (R1*, R2*), as shown in FIG. 7B, coordinates (K*, L*) corresponding to the coordinates (R1*, R2*) are identified in the blood vessel information coordinate system 83. Thus, depth data K* and hemoglobin index data L* are obtained with respect to the pixel in the predetermined position in the blood vessel area.

Figure 8A:
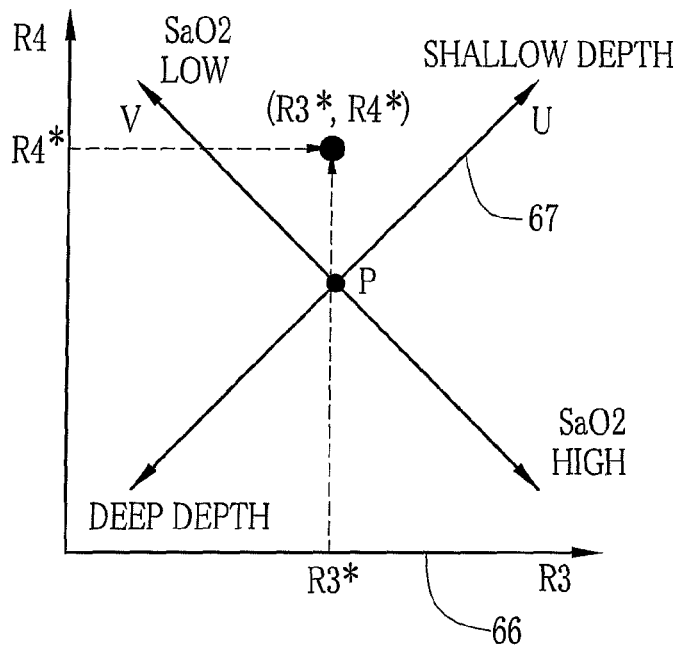
FIG. 8A is a graph in which coordinates (R3*, R4*) of the third and fourth brightness ratios are plotted on a brightness coordinate system.
Figure 8B:
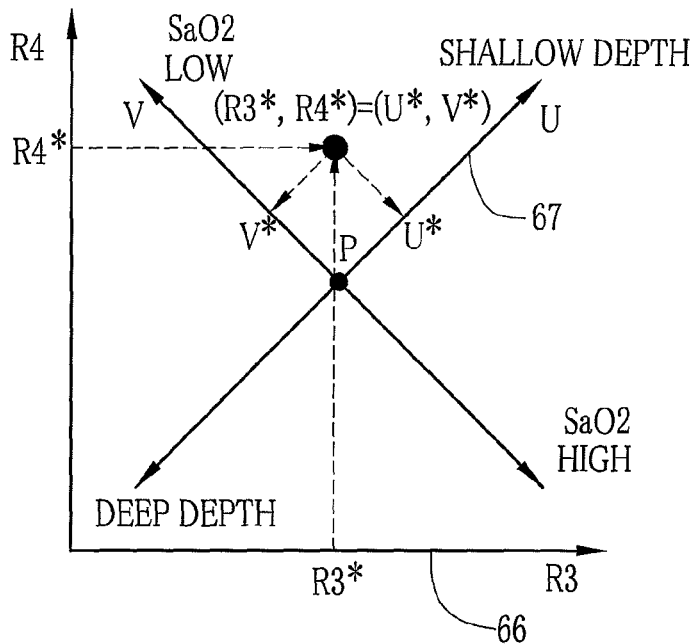
FIG. 8B is a graph that explains how to obtain coordinates (U*, V*) corresponding to the coordinates (R3*, R4*) on a blood vessel information coordinate system.

As shown in FIG. 8A, the depth and oxygen saturation calculator 69 plots in the brightness coordinate system 66 coordinates (R3*, R4*) that correspond to the third and fourth brightness ratios R3* and R4* being measurement values. After the plot of the coordinates (R3*, R4*), as shown in FIG. 8B, coordinates (U*, V*) corresponding to the coordinates (R3*, R4*) are identified in the blood vessel information coordinate system 67. Thus, depth data U* and oxygen saturation data V* are obtained with respect to the pixel in the predetermined position in the blood vessel area.

The depth image generator 63 has a color map (CM) 63a to assign color data to each pixel within the blood vessel area in accordance with the depth of the blood vessel. The color map 63a describes color assignment to clearly distinguish the depth of the blood vessel, in such a manner as to assign blue to the shallow blood vessel, green to the middle blood vessel, and red to the deep blood vessel, for example. The depth image generator 63 defines based on the color map 63a the color data corresponding to the depth data K* obtained by the depth and hemoglobin index calculator 62. The color data may be defined from the depth data U* obtained by the depth and oxygen saturation calculator 69.

After the color data is defined on every pixel within the blood vessel area, the depth image generator 63 reads out the normal image from the frame memory 56, and incorporates the color data into the read normal image. Thus, a blood vessel depth image is produced with the incorporation of the depth of the blood vessel. The produced blood vessel depth image is written to the frame memory 56. The color data may be incorporated into any of the first to third special images or a composition image produced from the first to third special images, instead of the normal image.

The hemoglobin index image generator 64 has a color map (CM) 64a to assign color data to each pixel within the blood vessel area in accordance with the degree of the hemoglobin index. The color map 64a describes color assignment to clearly distinguish the degree of the hemoglobin index, in such a manner as to assign red to the low hemoglobin index, gray to the middle hemoglobin index, and cyan to the high hemoglobin index, for example. The hemoglobin index image generator 64 defines based on the color map 64a the color data corresponding to the hemoglobin index data L* obtained by the depth and hemoglobin index calculator 62. The color data is incorporated into the normal image to produce a hemoglobin index image with artificial color. The generated hemoglobin index image is written to the frame memory 56, just as with the blood vessel depth image.

The oxygen saturation image generator 78 has a color map (CM) 78a to assign color data to each pixel within the blood vessel area in accordance with an oxygen saturation level. The color map 78a describes color assignment to clearly distinguish the oxygen saturation level, in such a manner as to assign cyan to the low oxygen saturation level, magenta to the middle oxygen saturation level, and yellow to the high oxygen saturation level, for example. The oxygen saturation image generator 78 defines based on the color map 78a the color data corresponding to the oxygen saturation data V* obtained by the depth and oxygen saturation calculator 69. The color data is incorporated into the normal image to produce the oxygen saturation image. The produced oxygen saturation image is written to the frame memory 56, just as with the blood vessel depth image.

Figure 9:
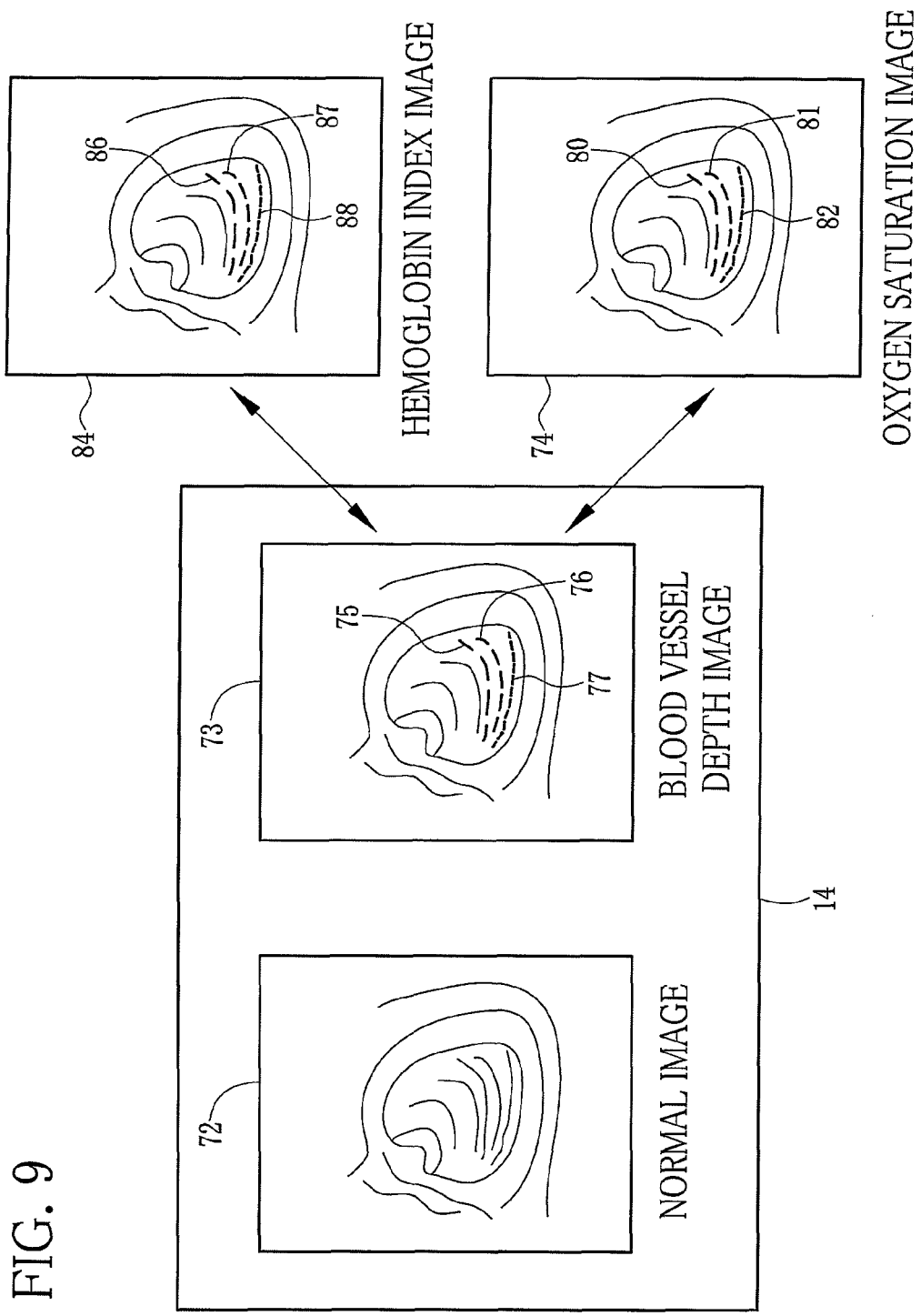
FIG. 9 is a plan view of a monitor on which only one of a blood vessel depth image, a hemoglobin index image, and an oxygen saturation image is displayed.

The display control circuit 58 reads out one or plural images from the frame memory 56, and displays the image or images on the monitor 14. There are various patterns of display. For example, as shown in FIG. 9, a normal image 72 is displayed on a half of the monitor 14, and one of a blood vessel depth image 73, a hemoglobin index image 84, and an oxygen saturation image 74 chosen by an image switching button 68 (see FIG. 2) may be displayed on the remaining half of the monitor 14. In the blood vessel depth image 73 of FIG. 8, a blood vessel image 75 is colored blue for indicating the shallow blood vessel, and a blood vessel image 76 is colored green for indicating the middle blood vessel, and a blood vessel image 77 is colored red for indicating the deep blood vessel. In the hemoglobin index image 84, a blood vessel image 86 is colored red for indicating the low hemoglobin index, and a blood vessel image 87 is colored gray for indicating the middle hemoglobin index, and a blood vessel image 88 is colored cyan for indicating the high hemoglobin index. In the oxygen saturation image 74, a blood vessel image 80 is colored cyan for indicating the low oxygen saturation level, and a blood vessel image 81 is colored magenta for indicating the middle oxygen saturation level, and a blood vessel image 82 is colored yellow for indicating the high oxygen saturation level.

Figure 10:
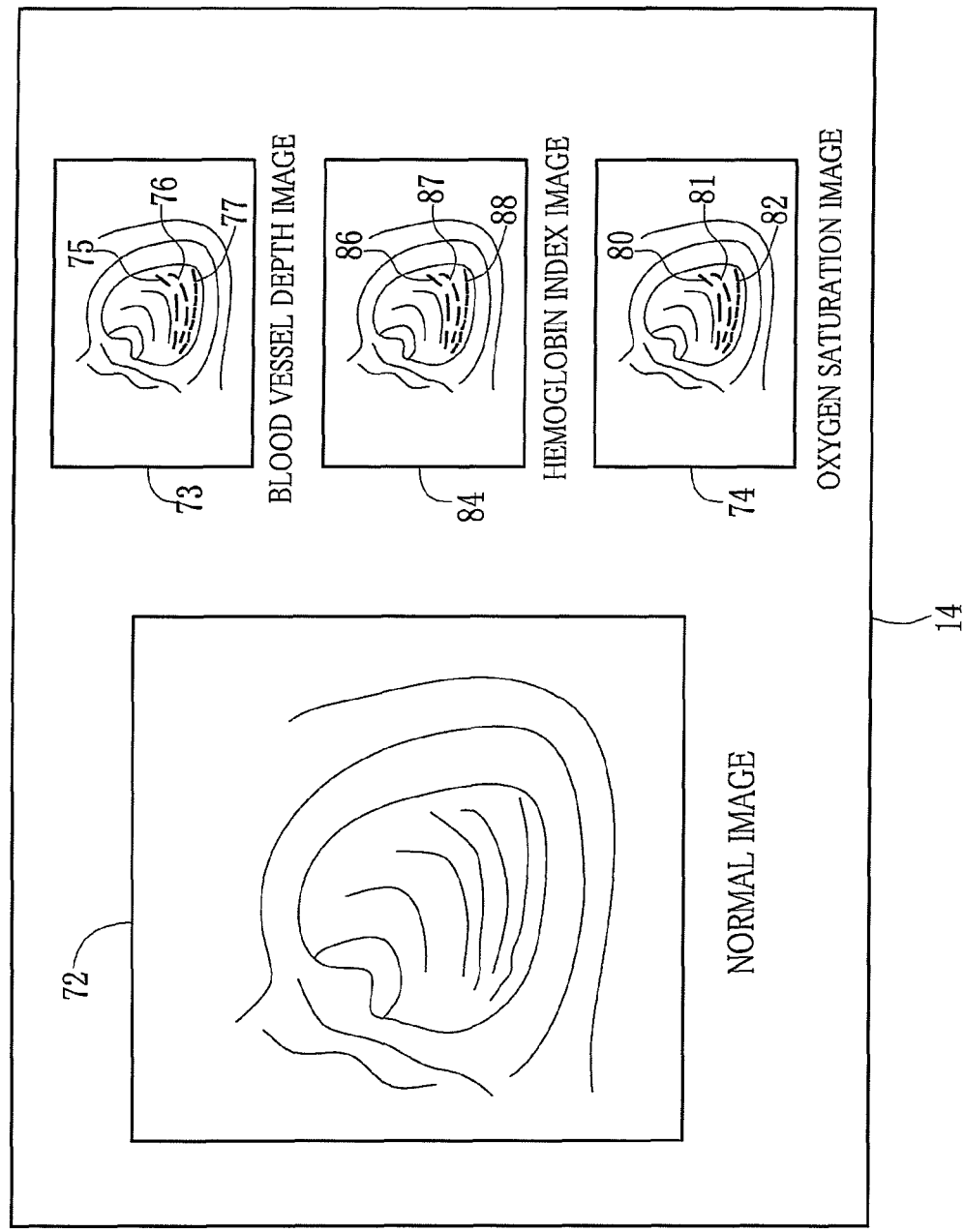
FIG. 10 is a plan view of the monitor on which all of the blood vessel depth image, the hemoglobin index image, and the oxygen saturation image are simultaneously displayed.
Figure 11:
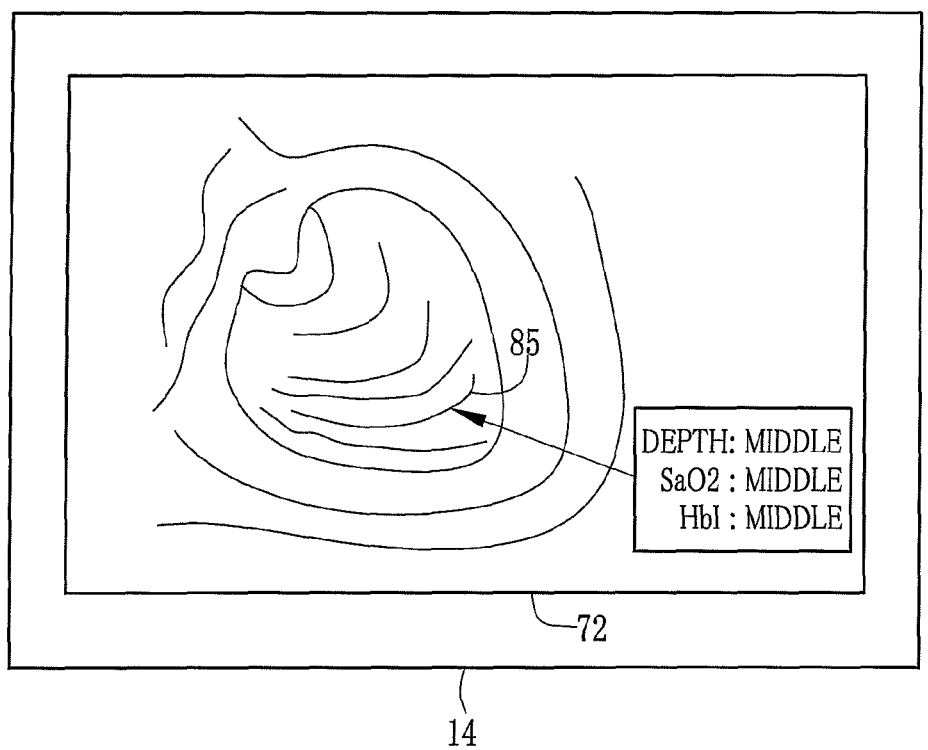
FIG. 11 is a plan view of the monitor on which blood vessel information including depth data, hemoglobin index data, and oxygen saturation data is displayed in text form.

All of the three images of the blood vessel depth image 73, the hemoglobin index image 84, and the oxygen saturation image 74 may be simultaneously displayed as shown in FIG. 10. Otherwise, as shown in FIG. 11, upon choosing an arbitrary blood vessel 85 by pointing with a mouse (not illustrated) or the like on the normal image 72 displayed on the monitor 14, the depth (D), the oxygen saturation level (SaO2), and the hemoglobin index (HbI) of the blood vessel 85 may be displayed in text. In the display pattern of FIG. 11, the blood vessel depth image 73, the hemoglobin index image 84, and the oxygen saturation image 74 are not displayed.

Figure 12:
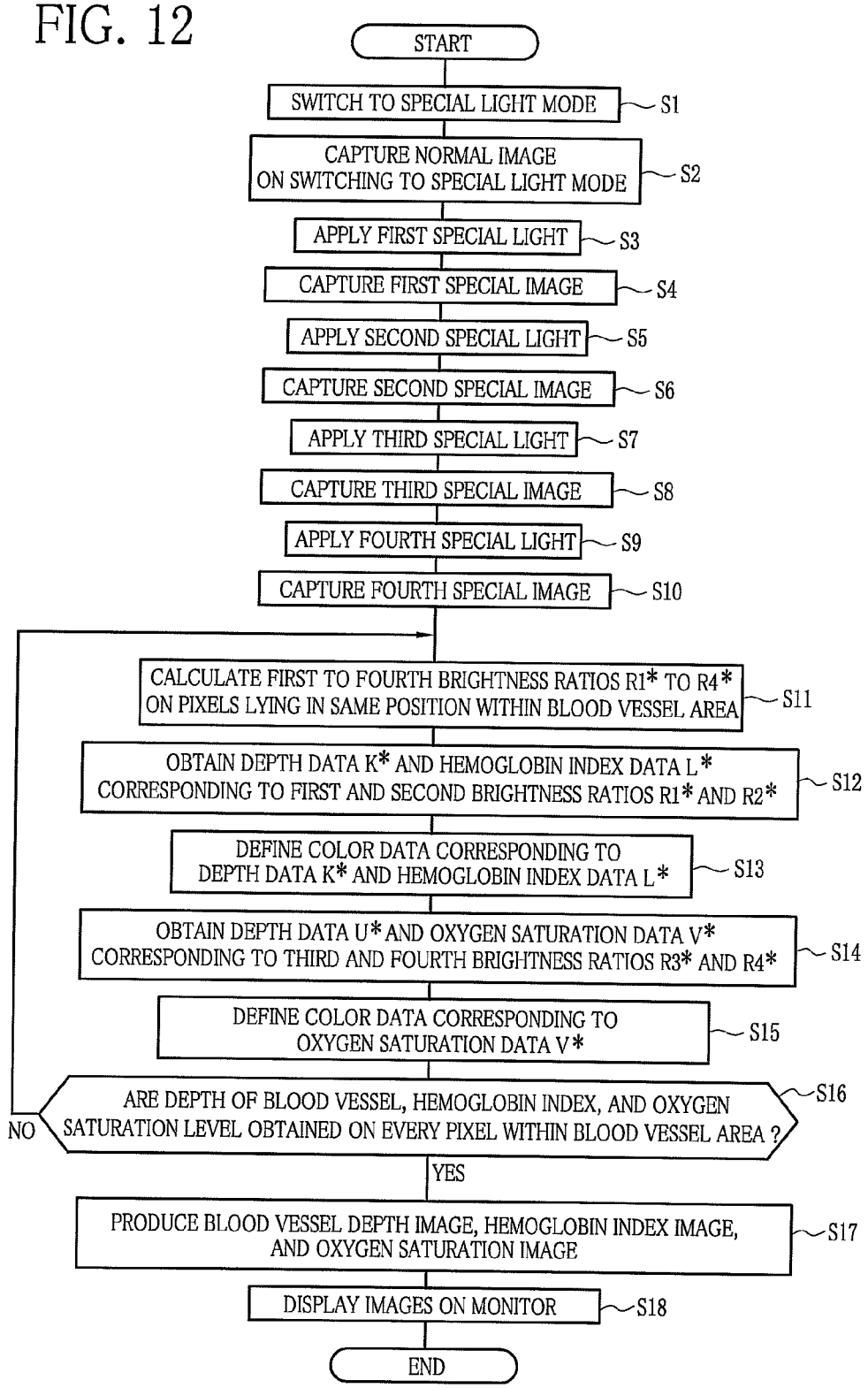
FIG. 12 is a flowchart of the electronic endoscope system.

The operation of the electronic endoscope system 10 will be described with referring to FIG. 12. The electronic endoscope system 10 is switched from the normal light mode to the special light mode (S1) by operation on a console 23. Upon switching to the special light mode, the normal image that is captured at the time of switching is written to the frame memory 56 (S2) for use in production of the blood vessel depth image, the hemoglobin index image, and the oxygen saturation image. The normal image captured before the operation of the console 23 may be used instead to produce the blood vessel depth image and the like.

Then, when the controller 59 sends a normal light application stop command to the shutter driver 32, the shutter driver 32 moves the shutter 31 from the retraction position to the insertion position to stop applying the normal light NL to the internal body part to be examined. Upon stopping application of the normal light NL, a special light application start command is issued from the controller 59 to the light source switch 37. Thus, the light source switch 37 turns on the first special light source 33 to apply the first special light L1 to the internal body part (S3). Upon application of the first special light L1, the controller 59 issues an image capture command to the imaging controller 46. Thus, the image is captured under the first special light L1 (S4), and the obtained first special image signal is sent through the AFE 45 to the DSP 55. In the DSP 55, the first special image is generated from the first special image signal. The generated first special image is written to the frame memory 56.

After the first special image is written to the frame memory 56, the light source switch 37 switches the light to be applied from the first special light L1 to the second special light L2 (S5), in response to a light source switching command from the controller 59. Then, the image is captured under the second special light L2 (S6), as with above, and the second special image is generated from the second special image signal. The generated second special image is written to the frame memory 56.

After the second special image is written to the frame memory 56, the light source switch 37 switches the light to be applied from the second special light L2 to the third special light L3 (S7), in response to the light source switching command from the controller 59. Then, the image is captured under the third special light L3 (S8), and the third special image is generated from the third special image signal. The generated third special image is written to the frame memory 56.

After the third special image is written to the frame memory 56, the light source switch 37 switches the light to be applied from the third special light L3 to the fourth special light L4 (S9), in response to the light source switching command from the controller 59. Then, the image is captured under the fourth special light L4 (S10), and the fourth special image is generated from the fourth special image signal. The generated fourth special image is written to the frame memory 56.

After the normal image and the first to fourth special images are written to the frame memory 56, the brightness ratio calculator 60 extracts the blood vessel area containing the blood vessel from each of the first to fourth special images. Then, the brightness ratio calculator 60 calculates the first brightness ratio R1* from the first and second special images, the second brightness ratio R2* from the third and second special images, the third brightness ratio R3* from the fourth and first special images, and the fourth brightness ratio R4* from the second and first special images, on the pixels lying in the same position within the blood vessel area (S11).

Next, the depth and hemoglobin index calculator 62 identifies in the blood vessel information coordinate system 83 the coordinates (K*, L*) corresponding to the first and second brightness ratios R1* and R2* being the measurement values, based on the correlation stored in the depth-hemoglobin index correlation memory 61. Thus, the depth data K* and the hemoglobin index data L* are obtained on the predetermined pixel within the blood vessel area (S12).

Upon obtainment of the depth data K* and the hemoglobin index data L*, the color data corresponding to the depth data K* is defined from the CM 63a of the depth image generator 63. The color data corresponding to the hemoglobin index data L* is defined from the CM 64a of the hemoglobin index image generator 64 (S13). The defined color data is written to a RAM (not illustrated) in the processor unit 12.

Next, the depth and oxygen saturation calculator 69 identifies in the blood vessel information coordinate system 67 the coordinates (U*, V*) corresponding to the third and fourth brightness ratios R3* and R4* being the measurement values, based on the correlation stored in the depth-oxygen saturation correlation memory 65. Thus, the depth data U* and the oxygen saturation data V* are obtained on the predetermined pixel within the blood vessel area (S14). The depth data U* is not used in this embodiment, because it is the same as the depth data K* described above.

Then, the color data corresponding to the oxygen saturation data V* is defined from the CM 78a of the oxygen saturation image generator 78 (S15). The defined color data is written to the RAM (not illustrated) of the processor unit 12.

By repeating the above steps S11 to S15 until step S16 becomes YES, the depth data K*, the hemoglobin index data L*, and the oxygen saturation data V* are obtained on every pixel within the blood vessel area. Also, the color data corresponding to each of the depth data K*, the hemoglobin index data L*, and the oxygen saturation data V* is defined.

After the depth data, the hemoglobin index data, and the oxygen saturation data, and the color data corresponding thereto are obtained on every pixel within the blood vessel area (YES in S16), the depth image generator 63 reads out the normal image from the frame memory 56. The depth image generator 63 incorporates the color data written to the RAM into the normal image to produce the blood vessel depth image. The hemoglobin index image generator 64 produces the hemoglobin index image in a like manner as the blood vessel depth image. The oxygen saturation image generator 78 also produces the oxygen saturation image in a like manner (S17). The produced blood vessel depth image, hemoglobin index mage, and oxygen saturation image are written to the frame memory 56.

The display control circuit 58 reads each image from the frame memory 56, and displays the normal image 72, the blood vessel depth image 73, the hemoglobin index image 84, and the oxygen saturation image 74 on the monitor 14 (S18) as shown in FIG. 9 or 10. In FIG. 9, one of the blood vessel depth image 73, the hemoglobin index image 84, and the oxygen saturation image 72 is displayed on the monitor 14 together with the normal image 72. In FIG. 10, four images of the normal image 72, the blood vessel depth image 73, the hemoglobin index image 84, and the oxygen saturation image 74 are simultaneously displayed on the monitor 14.

Second Embodiment

Figure 13:
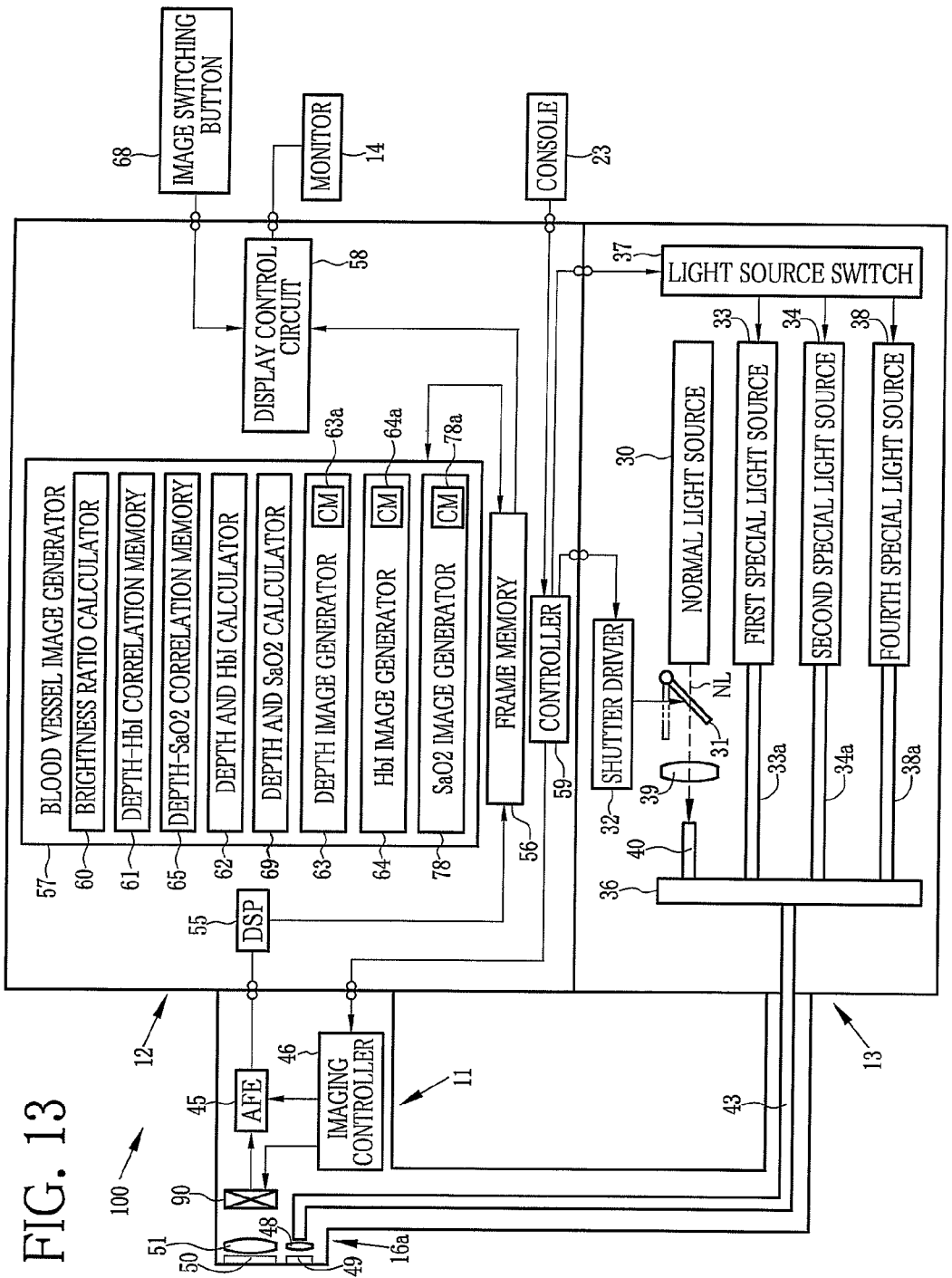
FIG. 13 is a block diagram of the electronic endoscope system according to a second embodiment.
Figure 14:
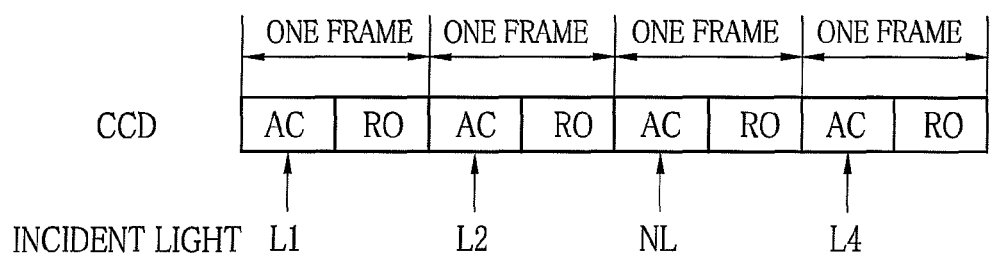
FIG. 14 is an explanatory view of imaging operation of the CCD in the special light mode.

In an electronic endoscope system 100 according to a second embodiment, as shown in FIG. 13, a CCD 90 is a color CCD having R, G, and B pixels. Furthermore, in the special light mode, the normal light NL is applied to the internal body part to be examined instead of the third special light L3, as shown in FIG. 14. The second brightness ratio R2 is calculated with use of an image signal that is obtained from the G pixels of the CCD 90 in application of the normal light NL. The electronic endoscope system 100 according to the second embodiment does not use the third special light L3, and hence does not have the third special light source. Since the other components of the electronic endoscope system 100 according to the second embodiment are substantially the same as those of the first embodiment, the description thereof will be omitted.

Figure 15:
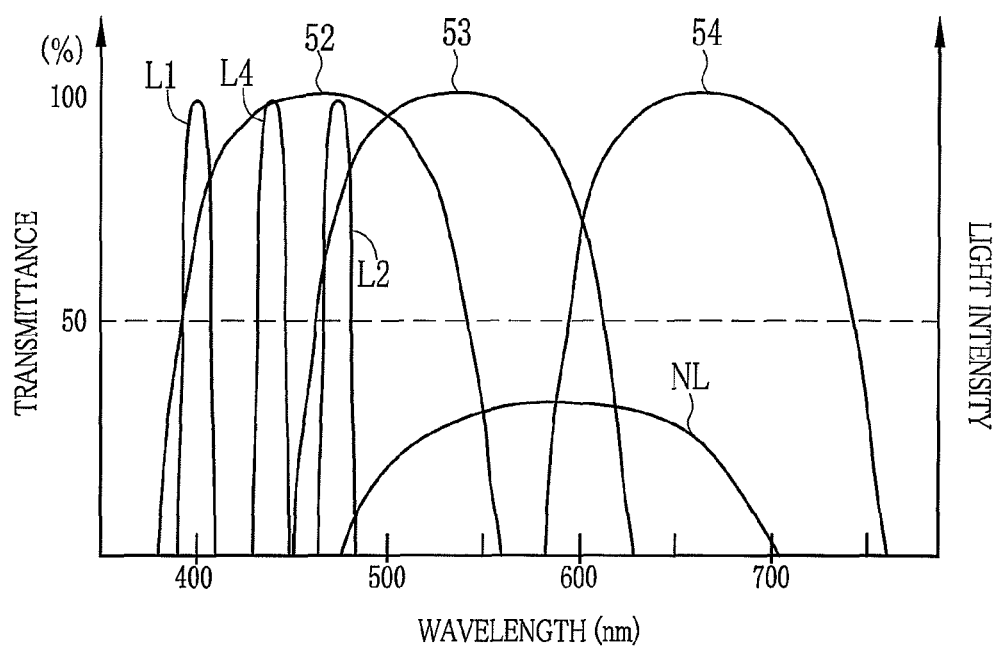
FIG. 15 is a graph showing the spectral transmittance of each of R, G, and B color filters and the spectral intensity of normal light and first, second, and fourth special light.

The R, G, and B pixels of the CCD 90 have R, G, and B color filters, respectively. Referring to FIG. 15, the R, G, and B color filters have spectral transmittance 54, 53, and 52, respectively. Since the normal light NL has wavelengths of approximately 470 to 700 nm, all of the R, G, and B pixels sense the normal light NL. On the other hand, since the first special light L1 has wavelengths of 405±10 nm, only the B pixels sense the first special light L1. Since the second special light L2 has wavelengths of 470±10 nm, the B and G pixels sense the second special light L2, while the R pixels do not sense it. Since the fourth special light L4 has wavelengths of 440±10 nm, only the B pixels sense the fourth special light L4.

As described above, in the CCD 90, the sensing pixels depend on the type of the light applied. Therefore, a method for calculating the first to fourth brightness ratios R1 to R4 is different from that of the first embodiment. In the second embodiment, the first brightness ratio R1 is calculated by Log(B1/B2), based on a brightness value B1 obtained by the B pixel of the CCD 90 under the first special light L1 and a brightness value B2 obtained by the B pixel under the second special light L2. The second brightness ratio R2 is calculated by Log(Broad_G/B2), based on the brightness value B2 obtained by the B pixel under the second special light L2 and a brightness value Broad_G obtained by the G pixel under the normal light NL.

The third brightness ratio R3 is calculated by B4/B1, based on the brightness value B1 obtained by the B pixel of the CCD 90 under the first special light L1 and a brightness value B4 obtained by the B pixel under the fourth special light L4. Furthermore, the fourth brightness ratio R4 is calculated by B2/B1, based on the brightness ratio B2 obtained by the B pixel of the CCD 90 under the second special light L2 and the brightness value B1 obtained by the B pixel under the first special light L1.

Third Embodiment

Figure 16:
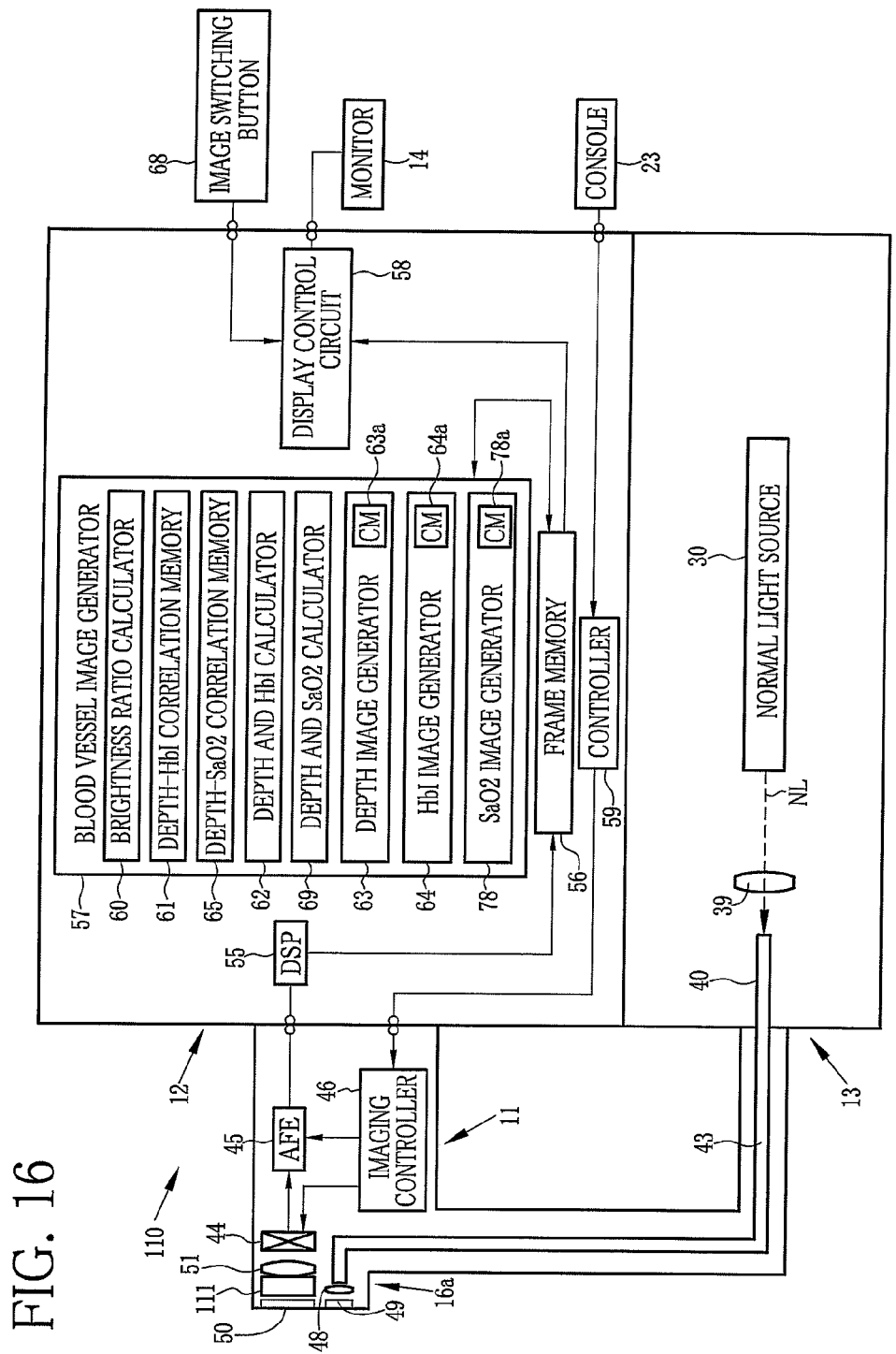
FIG. 16 is a block diagram of the electronic endoscope system according to a third embodiment.

In a third embodiment, the first to fourth special light sources are not provided. Instead, an acoustic-optical tunable filter separates reflected light of the normal light NL into first to fourth special light L1 to L4. As shown in FIG. 16, an electronic endoscope system 110 according to the third embodiment is the same as the electronic endoscope system 10 of the first embodiment, except for provision of the acoustic-optical tunable filter 111 in the electronic endoscope 11 and elimination of the first to fourth special light sources 33 to 35 and 38.

The electronic endoscope 110 according to the third embodiment is provided with the acoustic-optical tunable filter 111 disposed between the imaging window 50 and the condenser lens 51. In the normal light mode, the acoustic-optical tunable filter 111 is not actuated, so that the normal light NL reflected from the internal body part to be examined is incident upon the CCD 44. In the special light mode, out of the normal light NL reflected from the internal body part, the acoustic-optical tunable filter 111 passes only light of a specific wavelength and blocks light of the other wavelengths to generate the first to fourth special light L1 to L4. The acoustic-optical tunable filter 111 selectively passes the first special light L1 initially, and then selectively passes the second special light L2, the third special light L3, and the fourth special light L4 in this order, but this order may be changeable. The acoustic-optical tunable filter 111 is connected to the imaging controller 46, and sends a spectroscopic signal to the imaging controller 46 whenever carrying out spectroscopy. Based on the spectroscopic signal, the imaging controller 46 issues the image capture command to the CCD 44. Thus, the CCD 44 captures the image whenever carrying out the spectroscopy, and hence outputs first to fourth spectroscopic image signals, as in the case of the first embodiment.

In the third embodiment, a special CCD may be used instead of provision of the acoustic-optical tunable filter 111 between the imaging window 50 and the condenser lens 51. This special CCD has first pixels that are provided with a filter for passing only the first special light L1 out of the normal light NL, the second pixels that are provided with a filter for passing only the second special light L2, the third pixels that are provided with a filter for passing only the third special light L3, and the fourth pixels that are provided with a filter for passing only the fourth special light L4.

Figure 17:
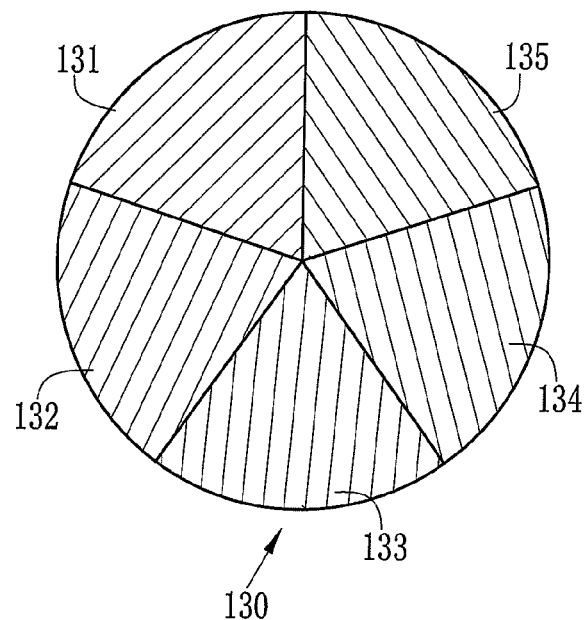
FIG. 17 is a schematic plan view of a rotary filter having a normal light transmission region and first to fourth special light transmission regions.

In the first embodiment, the first to fourth special light sources are used to generate the first to fourth special light L1 to L4. However, eliminating the provision of the first to fourth special light sources, a rotary filter 130 as shown in FIG. 17 may be disposed instead of the shutter 31 of FIG. 2 to extract the first to fourth special light L1 to L4. The rotary filter 130 includes a normal light transmission region 131 for passing the whole components of the normal light NL emitted from the normal light source 30, a first special light transmission region 132 for passing the component of the first special light L1 out of the normal light NL, a second special light transmission region 133 for passing the component of the second special light L2, a third special light transmission region 134 for passing the component of the third special light L3, and a fourth special light transmission region 135 for passing the component of the fourth special light L4. The rotary filter 130 is rotatable, so that one of the regions (filters) 131 to 135 is disposed in the optical path of the normal light source 30 in accordance with the light to be applied. Eliminating the normal light transmission region 131, the rotary filter 130 may be retracted from the optical path of the normal light source 30 in application of the normal light NL to the internal body part.

In the first embodiment, the images of four frames are captured in the special light mode, by capturing the image whenever each of the first to fourth special light L1 to L4 is applied. However, the first to fourth special light L1 to L4 may be simultaneously applied to the internal body part in order to reduce the number of the frames to be captured to one. To take the first to fourth special image signals out of a single image signal obtained by the simultaneous application of light, the special CCD describe above is usable.

In the first embodiment, while the normal light NL emitted from the normal light source is directly applied to the internal body part, the monochrome CCD captures the image, and the normal image is produced from the normal image signal obtained by the monochrome CCD. However, a method for producing the normal image is not limited to it.

Figure 18:
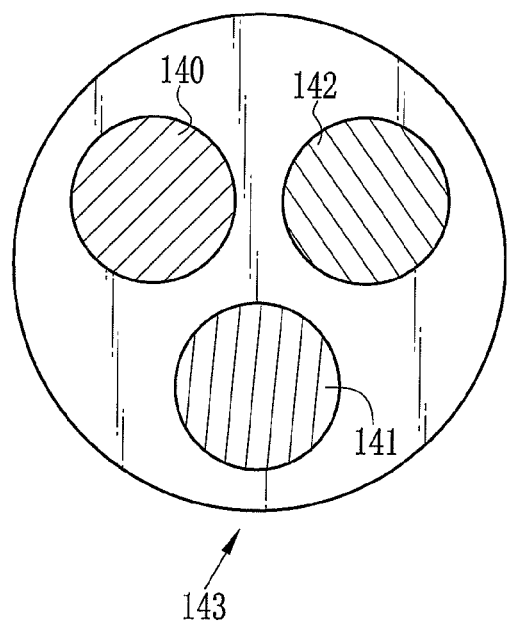
FIG. 18 is a schematic plan view of a rotary filter having B, G, and R color filters.

For example, the normal image may be produced by a frame sequential method. In the frame sequential method, a rotary filter 143 having B, G, and R three color filters 140 to 142, as shown in FIG. 18, is disposed in front of the normal light source. In production of the normal image, the rotary filter 143 is rotated so that the B color filter 140, the G color filter 141, and the R color filter 142 are successively disposed in the optical path of the normal light NL. By the rotation of the rotary filter 143, blue, green, and red light is successively applied to the internal body part.

Figure 19:
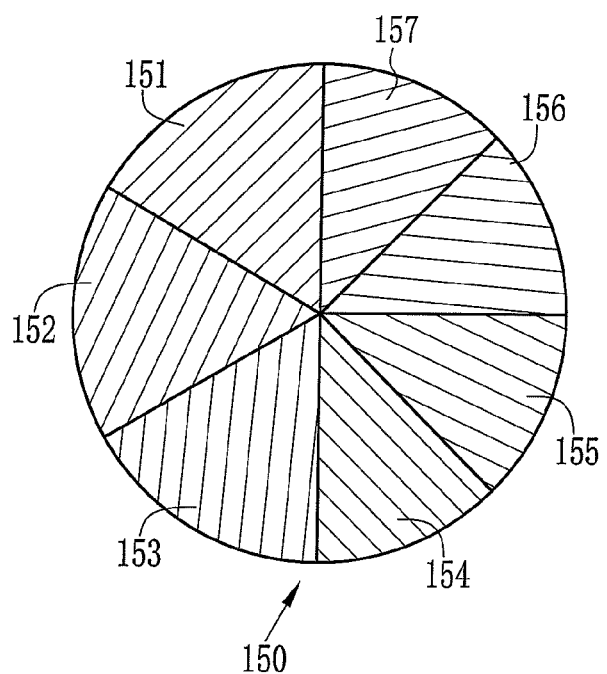
FIG. 19 is a schematic plan view of a rotary filter having the B, G, R color filters and the first to fourth special light transmission regions.

Whenever the light of each color is applied, the monochrome CCD captures the image, so that the image signals of three colors, that is, blue, green, and red image signals are obtained. The color normal image is produced from the image signals of three colors. In the frame sequential method, there is a time lag among the image signals of three colors, because the image is captured whenever the light of each color is applied. Thus, if the internal body part or the insert section of the electronic endoscope moves during switching the color of the light to be applied, the produced normal image is blurred. In the frame sequential method, as shown in FIG. 19, a rotary filter 150 may be provided with B, G, and R three color filters 151 to 153 similar to those of FIG. 18, and first to fourth special light transmission regions 154 to 157 similar to those of FIG. 17. This eliminates the need for providing the first to fourth special light sources 33 to 35 and 38 in the light source unit 13.

Instead of the frame sequential method, a simultaneous method may be used to produce the normal image. The simultaneous method uses the color CCD having the B, G, and R pixels the sensitivity of which depends on the wavelength. To produce the normal image, the normal light NL is directly applied to the internal body part, and the normal light NL reflected from the body part is received by the color CCD. Thus, the blue, green, and red image signals are simultaneously outputted from the B, G, and R pixels, respectively. The normal image is produced from these image signals of three colors. In the simultaneous method, as described above, the time lag does not occur because the image signals of three colors are outputted at the same time. Accordingly, even if the internal body part or the insert section of the electronic endoscope moves, the normal image is not blurred. As the color CCD, a complementary-color CCD having a filter of complimentary three colors of C (cyan), M (magenta), and Y (yellow) may be used, instead of the primary-color CCD having a filter of primary colors of R, G, and B.

The present invention is applicable not only to the insertable electronic endoscope having the insert section or the like, but also to a capsule endoscope in which the image sensor such as the CCD is contained in a capsule.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic endoscope system comprising:
    a light applying section for applying at least three types of narrow band light having wavelengths within 400 nm to 600 nm as illumination light to an internal body part containing a blood vessel, two types of the illumination light out of the three types of the illumination light being narrow blue band light and narrow green band light;
    an image sensor for capturing an image of the internal body part irradiated with the illumination light;
    a blood vessel information obtaining section for obtaining blood vessel information based on a narrow band signal corresponding to the three types of the narrow band light, the blood vessel information including a depth of the blood vessel and a hemoglobin index,
    a brightness ratio calculating section for calculating a first brightness ratio between the first narrow blue band signal and the second narrow blue band signal, and a second brightness ratio between the third narrow green band signal and the second narrow blue band signal; and a memory for storing in advance a correlation between the depth of the blood vessel and the hemoglobin index with respect to the first and second brightness ratios, wherein the three types of the illumination light includes first narrow blue band light, second narrow blue band light, and third narrow green band light; and the narrow band signal corresponding to the three types of the narrow band light includes a first narrow blue band signal, a second narrow blue band signal, and a third narrow green band signal;

wherein, the blood vessel information obtaining section obtains based on the correlation stored in the memory the depth of the blood vessel and the hemoglobin index from the first and second brightness ratios.

2. The electronic endoscope system according to claim 1, wherein the memory stores in advance a correlation between a brightness coordinate system representing the first and second brightness ratios and a blood vessel information coordinate system representing the depth of the blood vessel and the hemoglobin index; and the blood vessel information obtaining section plots coordinates of the first and second brightness ratios on the brightness coordinate system, and then reads out from the blood vessel information coordinate system coordinates of the depth of the blood vessel and the hemoglobin index corresponding to the plotted coordinates, to identify values of the depth of the blood vessel and the hemoglobin index.

3. The electronic endoscope system according to claim 1, wherein the first narrow blue band light has wavelengths of 405±10 nm, and the second narrow blue band light has wavelengths of 470±10 nm, and the third narrow green band light has wavelengths of 560±10 nm.

4. The electronic endoscope system according to claim 1, wherein the light applying section selectively emits the first narrow blue band light, the second narrow blue band light, and the third narrow green band light; and the image sensor captures the image under the first narrow blue band light to obtain the first narrow blue band signal of one frame, and captures the image under the second narrow blue band light to obtain the second narrow blue band signal of one frame, and captures the image under the third narrow green band light to obtain the third narrow green band signal of one frame.

5. The electronic endoscope system according to claim 1, wherein the light applying section includes:

a white light source for emitting white broad band light; and a wavelength band limiting section disposed between the white light source and the image sensor, the wavelength band limiting section selectively extracting the three types of the narrow band light out of the broad band light.

6. The electronic endoscope system according to claim 5, wherein the wavelength band limiting section is an acoustic-optical tunable filter.

7. The electronic endoscope system according to claim 5, wherein the wavelength band limiting section is a rotary filter having a plurality of filters for selectively passing the three types of the narrow band light.

8. The electronic endoscope system according to claim 1, wherein the illumination light further includes fourth narrow blue band light having wavelengths of 440±10 nm, and an oxygen saturation level in the blood vessel is obtained as the blood vessel information from a fourth narrow blue band signal corresponding to the fourth narrow blue band light.

9. A processor unit connected to an electronic endoscope comprising:

a receiving section for receiving an image signal from the electronic endoscope, the image signal being obtained by an image sensor for capturing an image of an internal body part containing a blood vessel, while the internal body part is irradiated with at least three types of narrow band light as illumination light, two types of the illumination light out of the three types of the illumination light being narrow blue band light and narrow green band light;

a blood vessel information obtaining section for obtaining blood vessel information based on a narrow band signal corresponding to the three types of the narrow band light, the blood vessel information including a depth of the blood vessel and a hemoglobin index, a brightness ratio calculating section for calculating a first brightness ratio between the first narrow blue band signal and the second narrow blue band signal, and a second brightness ratio between the third narrow green band signal and the second narrow blue band signal; and a memory for storing in advance a correlation between the depth of the blood vessel and the hemoglobin index with respect to the first and second brightness ratios, wherein the three types of the illumination light includes first narrow blue band light, second narrow blue band light, and third narrow green band light; and the narrow band signal corresponding to the three types of the narrow band light includes a first narrow blue band signal, a second narrow blue band signal, and a third narrow green band signal;

wherein, the blood vessel information obtaining section obtains based on the correlation stored in the memory the depth of the blood vessel and the hemoglobin index from the first and second brightness ratios.

10. A method for obtaining blood vessel information comprising the steps of:

applying at least three types of narrow band light having wavelengths within 400 nm to 600 nm as illumination light to an internal body part containing a blood vessel, two types of the illumination light out of the three types of the illumination light being narrow blue band light and narrow green band light;

capturing an image of the internal body part irradiated with the illumination light; and obtaining blood vessel information based on a narrow band signal corresponding to the three types of the narrow band light, the blood vessel information including a depth of the blood vessel and a hemoglobin index, a brightness ratio calculating section for calculating a first brightness ratio between the first narrow blue band signal and the second narrow blue band signal, and a second brightness ratio between the third narrow green band signal and the second narrow blue band signal; and a memory for storing in advance a correlation between the depth of the blood vessel and the hemoglobin index with respect to the first and second brightness ratios, wherein the three types of the illumination light includes first narrow blue band light, second narrow blue band light, and third narrow green band light; and the narrow band signal corresponding to the three types of the narrow band light includes a first narrow blue band signal, a second narrow blue band signal, and a third narrow green band signal;

wherein, the blood vessel information obtaining section obtains based on the correlation stored in the memory the depth of the blood vessel and the hemoglobin index from the first and second brightness ratios.

* * * * *